United States Patent
D'Elia et al.

(10) Patent No.: US 9,586,926 B2
(45) Date of Patent: Mar. 7, 2017

(54) METHODS OF MAKING ALKYLENE CARBONATES AND METHODS OF CONVERTING $CO_2$

(71) Applicant: King Abdullah University of Science and Technology, Thuwal (SA)

(72) Inventors: Valerio D'Elia, Thuwal (SA); Jeremie D. A. Pelletier, Thuwal (SA); Jean-Marie Basset, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 14/902,880

(22) PCT Filed: Jul. 8, 2014

(86) PCT No.: PCT/IB2014/002257
§ 371 (c)(1),
(2) Date: Jan. 5, 2016

(87) PCT Pub. No.: WO2015/004536
PCT Pub. Date: Jan. 15, 2015

(65) Prior Publication Data
US 2016/0145233 A1    May 26, 2016

Related U.S. Application Data

(60) Provisional application No. 61/843,969, filed on Jul. 9, 2013.

(51) Int. Cl.
*C07D 317/08* (2006.01)
*C07D 317/36* (2006.01)

(52) U.S. Cl.
CPC .................. *C07D 317/36* (2013.01)

(58) Field of Classification Search
CPC .................................................. C07D 317/36

USPC .......................................................... 549/230
See application file for complete search history.

(56) References Cited

U.S. PATENT DOCUMENTS

| 6,870,004 B1 | 3/2005 | Nguyen et al. |
| 2006/0089252 A1 | 4/2006 | Coates et al. |
| 2006/0094893 A1 | 5/2006 | Srinivas et al. |

OTHER PUBLICATIONS

D'Elia et al. ChemCatChem 2015, 7, 1906-1917.*
Ion et al. Applied Catalysis A: General 363 (2009) 40-44.*
Robert L. Paddock et al: "Chiral (salen)Coiii catalyst for the synthesis of cyclic carbonates" Electronic supplementary information (ESI) available: general experimental procedures and analytical data for new compounds. See http://www.rsc.orgjsuppdatajccjb4/b401543f/,Chemical Communications, No. 14, Jan. 1, 2004 (Jan. 1, 2004), p. 1622, XP055157866, ISSN: 1359-7345, DOI: 10.1039/b401543f.
Christopher J. Whiteoak et al: "A Powerful Aluminum Catalyst for the Synthesis of Highly Functional Organic Carbonates", Journal of the American Chemical Society, vol. 135, No. 4, Jan. 30, 2013 (Jan. 30, 2013), pp. 1228-1231, XP055157867, ISSN: 0002-7863, DOI: 10.1021jja311053h.
Christopher J. Whiteoak et al: "An Efficient Iron Catalyst for the Synthesis of Five- and Six-Membered Organic Carbonates under Mild Conditions", Advanced Synthesis & Catalysis, vol. 354, No. 2-3, Feb. 9, 2012 (Feb. 9, 2012), pp. 469-476, XP055157868, ISSN: 1615-4150, DOI: 10.1002/adsc.201100752.
International Search Report and Written Opinion of Application No. PCT/IB2014/002257 dated Dec. 22, 2014 (11 pages).
Ion, Angelica, et al. "Sc and Zn-catalyzed synthesis of cyclic carbonates from CO 2 and epoxides." Applied Catalysis A: General 363.1 (2009): 40-44.

* cited by examiner

*Primary Examiner* — Nizal Chandrakumar
(74) *Attorney, Agent, or Firm* — Thomas | Horstemeyer, LLP

(57) ABSTRACT

Embodiments of the present disclosure provide for a method of making an alkylene carbonate, catalysts, methods of converting $CO_2$ to an alkylene carbonate, and the like.

9 Claims, No Drawings

METHODS OF MAKING ALKYLENE CARBONATES AND METHODS OF CONVERTING CO₂

CROSS-REFERENCE TO RELATED APPLICATIONS

This application is the National Stage of International Application No. PCT/IB2014/002257, filed 8 Jul. 2014, which claims the benefit of and priority to U.S. Provisional Application No. 61/843,969, filed on 9 Jul. 2013, having the title "METHODS OF MAKING ALKYLENE CARBONATES AND METHODS OF CONVERTING $CO_2$", the contents of all of which are incorporated by reference as if fully set forth herein.

BACKGROUND

Around 30 Gt of $CO_2$ are released every year as an effect of human activities, mostly because of fossil fuel combustion. The huge amount of $CO_2$ accumulating in the atmosphere since the beginning of the industrial era represents an inexpensive, ubiquitous and oil-free source of carbon for the chemical industry, as well as an environmental threat, given the high global warming potential of $CO_2$. Therefore, the conversion of waste $CO_2$ into value-added chemicals would be extremely advantageous. Nevertheless, as power generation and $CO_2$ emission are unavoidably connected to fossil fuel combustion, only a process able to convert $CO_2$ efficiently under mild conditions of temperature and pressure (i.e. little to no energy input required) could act as actual $CO_2$ recycling with a positive C-balance. The process should preferentially be carried out directly from a stream of industrial flue gas to avoid the energetic penalty associated with $CO_2$ purification.

In this context, the exothermic reaction between epoxides and $CO_2$ to yield cyclic carbonates represents an active field of research. Cyclic carbonates such as ethylene or propylene carbonate represent key intermediates towards the synthesis of dimethyl carbonate and glycols (e.g., the Asahi-Kasei process, route to polycarbonates). Moreover, ethylene and propylene carbonate are useful highly polar solvents for a wide range of applications including as solvents for electrolytes in batteries and for the painting industry.

Cyclic carbonates are generally produced by the reaction of epoxides and $CO_2$ in the presence of metal halides and tetraalkylammonium salts. This process typically takes place at temperatures higher than 120° C. and at pressure above 40 bar and therefore is a net $CO_2$ producer. Alternatively, cyclic carbonates can be prepared from phosgene and glycols. This process presents low yields, produces corrosive HCl gas and uses a very toxic reagent such as phosgene which is considered a weapon of mass destruction (WMD).

There is currently a strong effort by most industrialized countries to reduce $CO_2$ emissions; International treaties such as the Kyoto Protocol have been signed by most UN member countries and mechanisms have been set in place to reward countries and firms able to abate emissions through the creation of quota systems and tradable emission credits. However no viable catalytic system existed so far for the conversion of $CO_2$ and alkylene oxides at ambient temperature and at sub-atmospheric $CO_2$ pressure under batch conditions or directly from a stream of diluted $CO_2$ gas.

Therefore, there is a need to overcome the deficiencies of current technology.

SUMMARY

Embodiments of the present disclosure provide for a method of making an alkylene carbonate, catalysts, methods of converting $CO_2$ to an alkylene carbonate, and the like.

One exemplary embodiment of a method, among others, includes the following reaction:

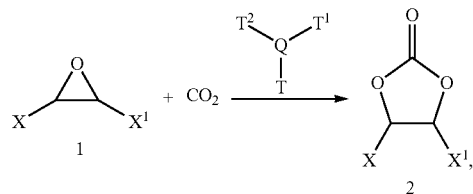

wherein X and $X^1$ are each independently selected from: a linear or branched, substituted or unsubstituted alkyl group; a substituted or unsubstituted aryl group; a substituted or unsubstituted cyclic group; a substituted or unsubstituted heteroaryl group; $C_xH_{2x}R$; OR; H; $NR_2$; $SR_2$; $SiR_2$; Cl; F; Br; I; B; $PR_2$; or SeR; wherein x is 1 to 10; wherein T, $T^1$, and $T^2$ are each independently selected from: F, Cl, Br, I, OR, $SR_2$, $NR_2$, $PR_2$, or, SeR; wherein each R is independently selected from: hydrogen; a linear or branched, substituted or unsubstituted alkyl group; a substituted or unsubstituted aryl group; a substituted or unsubstituted cyclic group; or a substituted or unsubstituted heteroaryl group; wherein Q is selected from scandium, yttrium, or lanthanum; and wherein $CO_2$ represents $CO_2$ or a mixture of gases containing $CO_2$.

In an embodiment, the reaction can include a co-catalyst as shown below:

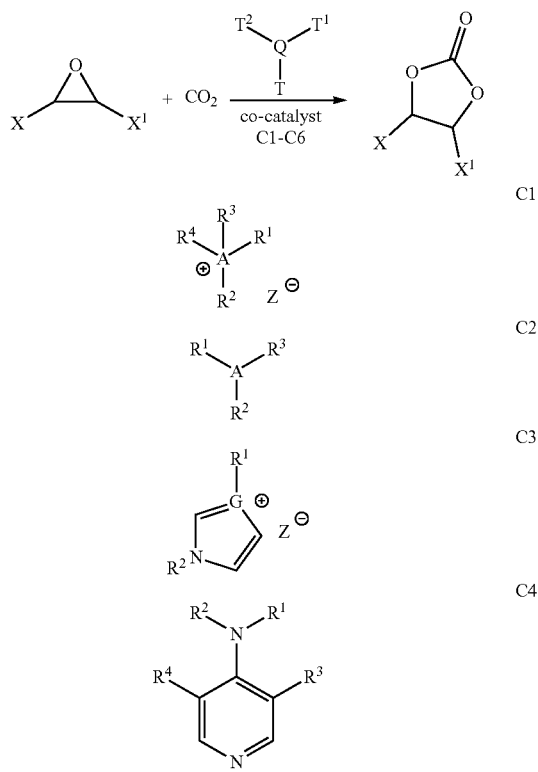

C5

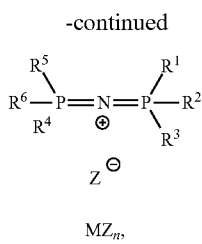

C6

MZ$_n$, wherein A is selected from N or P; wherein Z is selected from a halogen atom or from one of the following groups: Br$_3$, OR', SR', NO$_3$, SO$_3$, SO$_4$, R'SO$_3$, ClO$_4$, BF$_4$, R'CX$_3$COO, N$_3$, or CN, wherein each R' is independently selected from: H; a linear or branched, substituted or unsubstituted alkyl; a substituted or unsubstituted aryl; a substituted or unsubstituted cyclic group; or a substituted or unsubstituted heteroaryl; wherein X' is H, Cl, or F; wherein R$^1$, R$^2$, R$^3$, R$^4$, R$^5$, and R$^6$ are each independently selected from a linear or branched, substituted or unsubstituted alkyl; a substituted or unsubstituted aryl; a substituted or unsubstituted cyclic group; or a substituted or unsubstituted heteroaryl; wherein G is selected from N or S; and wherein M is selected from Li, Na, K, Sr, Mg, Al, or Ca.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "substituted" refers to any one or more hydrogens on the designated atom that can be replaced with a selection from the indicated group, provided that the designated atom's normal valence is not exceeded.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkanes, alkene, and alkynes, and alkyl, alkenyl, and alkynyl groups for example.

As used herein, "alkyl" or "alkyl group" refers to a linear or branched saturated aliphatic hydrocarbon having from 1 to 10 carbons. Examples of alkyl include, but are not limited to methyl, iso-propyl, sec-butyl, t-butyl, and iso-pentyl.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorus containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which includes carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a heteroatom if the resulting compound is stable.

The expression "dynamic conditions with respect to a reaction component" indicates that the given reaction component is continuously or progressively introduced into the reaction vessel or reactor containing the catalyst at a defined average flow rate and it is constantly removed or allowed to flow out from the reaction vessel at a defined flow rate. The stream of unconsumed reagent may or may not contain part of the other reaction components or products.

General Discussion

Embodiments of the present disclosure provide for a method of making an alkylene carbonate, catalysts, methods of converting $CO_2$ to an alkylene carbonate, and the like. Embodiments of the present disclosure provide for a simple, readily available, and inexpensive catalytic system that can convert $CO_2$ into value-added chemicals under extremely mild conditions of temperature and pressure and at low $CO_2$ concentrations under batch or under dynamic conditions with respect to $CO_2$.

An exemplary method uses a catalyst that can couple $CO_2$ and epoxides under ambient conditions and at low $CO_2$ pressure and concentration. As a result, methods of the present disclosure can have the effect of saving considerable amounts of energy, reducing $CO_2$ emissions, and simplifying the production setup by removing the need for high pressure/high temperature reactors.

In an embodiment, methods of the present disclosure could be implemented into suitable reactors able to use $CO_2$ directly at the place of production (for example, from flue gas at a power plant). This implementation would simultaneously allow the facile synthesis of cyclic carbonates and the capture of $CO_2$ at the source of emission. Therefore, this method could be used along with traditional $CO_2$ capture systems for the direct recycling of the $CO_2$ captured, as well as in a stand-alone $CO_2$-capture/value-adding device.

In an embodiment, the method can be used in a system that generates $CO_2$, and the method can reduce the $CO_2$ emissions. In an embodiment, the $CO_2$-containing mixture of gases can be represented by industrial waste flue gas. In particular, the method can be used to produce alkylene carbonates from $CO_2$ and epoxides in chemical plants that produce alkylene carbonates as intermediates towards the synthesis of acyclic carbonates such as, but not limited to, dimethyl carbonate, diethyl carbonate, and diphenyl carbonate.

In an embodiment, the method can be illustrated in the following reaction sequence:

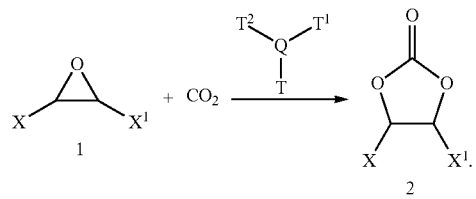

In an embodiment, the method can be used to make alkylene carbonates.

In an embodiment, the reaction can be conducted in a batch reactor at a partial pressure of about 0.001 MPa to about 20 MPa of $CO_2$ or about 0.01 MPa to about 5 MPa of $CO_2$ and the temperature of the reaction can be about −50° C. to about 250° C. or about 0° C. to about 150° C.

In an embodiment, the reaction can be conducted under dynamic conditions with respect to $CO_2$ by adding or bubbling a $CO_2$-containing mixture of gases ($CO_2$ concentration in the gas mixture: about 0.01% to about 100%) into a solution containing an epoxide, and the catalytic components can be at a temperature of about −50° C. to about 250° C. and at a pressure of about 0.01 to about 5 MPa.

In an embodiment, X and $X^1$ can each be independently selected from: an aliphatic group, an alkyl group (linear or branched, substituted or unsubstituted), an aryl group (substituted or unsubstituted), a cyclic group (substituted or unsubstituted), a heteroaryl group (substituted or unsubstituted), $C_xH_{2x}R$ (x can be 1 to 20), OR, H, $NR_2$, $SR_2$, $SiR_2$, Cl, F, Br, I, B, $PR_2$, or SeR.

In an embodiment, T, $T^1$, and $T^2$ can each be independently selected from: F, Cl, Br, I, OR, $SR_2$, $NR_2$, $PR_2$, or SeR. In an embodiment, Q can be selected from scandium, yttrium, or lanthanum. In an embodiment, $QTT^1T^2$ can be $YCl_3$ or $ScCl_3$.

In an embodiment, each R can be independently selected from: hydrogen, an aliphatic group, an alkyl group (linear or branched, substituted or unsubstituted), an aryl group (substituted or unsubstituted), a cyclic group (substituted or unsubstituted), or a heteroaryl group (substituted or unsubstituted). In an embodiment, X and $X^1$ can independently be hydrogen or a methyl group.

In another embodiment, the method can include a co-catalyst such as those described by the structures presented below (C1-C6) or a combination thereof. In an embodiment, the reaction can be represented by the following sequence:

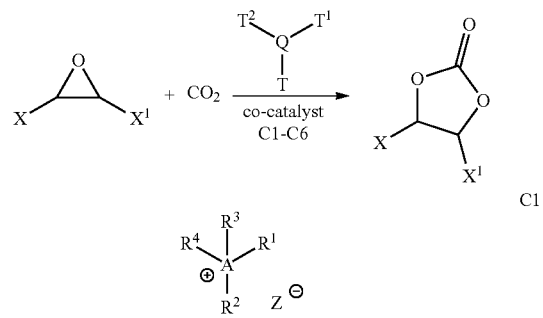

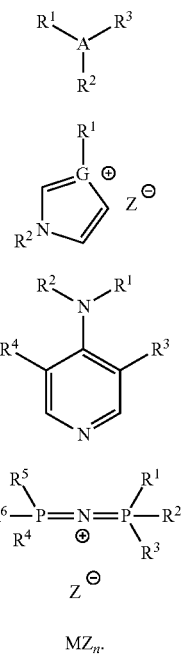

In an embodiment, A can be selected from N or P. In an embodiment, Z can be selected from a halogen atom or from one of the following groups: $Br_3$, OR' (R'=H, alkyl, aryl, cyclic, heteroaryl), SR' (R'=H, alkyl, aryl, cyclic, heteroaryl), $NO_3$, $SO_3$, $SO_4$, $RSO_3$ (R'=H, alkyl, aryl, cyclic, heteroaryl), $ClO_4$, $BF_4$, $RCX'_3COO$ (X'=H, Cl, F; R=H, alkyl, aryl, cyclic, heteroaryl), $N_3$, or CN (where each of the R' groups of Z can be substituted or unsubstituted).

In an embodiment, $R^1$, $R^2$, $R^3$, $R^4$, $R^5$, and $R^6$ can each be independently selected from: an alkyl (linear or branched), an aryl, a cyclic, or a heteroaryl group, and each can be substituted or unsubstituted. In an embodiment, G can be selected from N or S. In an embodiment, M can be selected from Li, Na, K, Sr, Mg, Al, or Ca.

In an embodiment, the co-catalyst can be selected from: tetrabutylammonium bromide or chloride, tert-butyl amine, triphenylphosphine, 4-dimethylaminopyridine, sodium or potassium iodide, 1-ethyl-3-methyl imidazolium bromide, bis(triphenylphosphine)iminium chloride or a combination thereof. In particular, the co-catalyst can be tetrabutylammonium bromide.

In an embodiment, alkylene carbonates can be used in solvents, lithium batteries, adhesives, paints, and plasticizers. In an embodiment, the alkylene carbonate can be used in other processes to produce useful reagents. For example, the alkylene carbonate can be used in the following reaction sequence, where R can be an alkyl group (linear or branched, substituted or unsubstituted), an aryl group (substituted or unsubstituted), a cyclic group (substituted or unsubstituted), a heteroaryl group (substituted or unsubstituted), and the like.

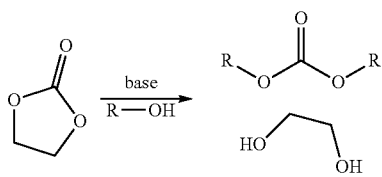

Examples

Now having described the embodiments of the disclosure, in general, the following examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Examples

1) $YCl_3$ (222.6 mg, 1.14 mmol; 1 equiv.) and TBAB (tetrabutylammonium bromide, 367.5 mg, 1.14 mmol; 1 equiv.) are dissolved in propylene oxide (8 mL, 114 mmol, 100 equiv.) at 25° C. under an atmosphere of Argon. $CO_2$ is added to this mixture until the total pressure in the reaction vessel reaches 0.2 MPa (partial $CO_2$ pressure: 0.1 MPa). The mixture is stirred for 3 h. The pressure in the vessel is kept constant at 0.2 MPa through the course of the experiment with the drop in pressure compensated by the addition of $CO_2$ through a pressure controller. After 3 h, the excess $CO_2$ is slowly vented and the conversion determined by comparing the corresponding peaks of the starting material and of the product in the $^1$H-NMR spectra of the mixture. Conversion of propylene oxide to propylene carbonate: 50% (Table 1, entry 1).

2) $YCl_3$ (22.3 mg, 0.114 mmol; 1 equiv.) and TBAB (tetrabutylammonium bromide, 48.4 mg, 0.15 mmol; 1.3 equiv.) are dissolved in propylene oxide (8 mL, 114 mmol, 1000 equiv.) at 25° C. under an atmosphere of Argon. The temperature of the reaction mixture is raised to 100° C. (5° C./min) while $CO_2$ is simultaneously pumped into the reaction vessel (0.07 MPa/min) until the total pressure reaches 1 MPa at 100° C. The mixture is stirred for 45 min. The pressure in the vessel is kept constant at 1 MPa through the course of the experiment, with the drop in pressure compensated by the addition of $CO_2$ through a pressure controller. After 45 h, the reactor is cooled to room temperature and the excess $CO_2$ slowly vented. The conversion is determined by comparing the corresponding peaks of the starting material and of the product in the $^1$H-NMR spectra of the mixture. Conversion of propylene oxide to propylene carbonate: 80%. (Table 1, entry 3).

3) (Dynamic conditions with respect to $CO_2$) $YCl_3$ (248 mg, 1.27 mmol; 1 equiv.) and TBAB (tetrabutylammonium bromide, 822 mg, 2.55 mmol; 2 equiv.) are dissolved in epichlorohydrin (2-(chloromethyl)oxirane) (10 mL, 127.5 mmol, 100 equiv.) at 22° C. under an atmosphere of Argon. A mixture of Ar and $CO_2$ (50% Ar; 50% $CO_2$ v/v, total flow rate 8 standard cm$^3$/min) is bubbled for 5 h into this mixture with stirring. After this period, the conversion to the corresponding cyclic carbonate was determined by comparing the corresponding peaks of the starting material and of the product in the $^1$H-NMR spectra of the mixture. Conversion: 33%. (Table 1, entry 9).

A number of additional examples on the application of Y, Sc, and La catalysts are reported in the following table; the reactions at 25° C. and 0.1 MPa $CO_2$ were carried out as in example 1, the other reactions as in example 2.

TABLE 1

$$R{-}\triangle\hspace{-0.5em}O + CO_2 \xrightarrow[\text{co-catalyst}]{\text{catalyst}} \underset{R}{\underset{|}{\bigcirc}}\hspace{-0.5em}\overset{O}{\underset{O}{\bigcirc}}$$

| Entry | R | catalyst/ (mol %) | co-catalyst/ (mol %)[a] | Temp. (° C.) | $CO_2$ pressure (MPa) | time (h) | Conversion (%)[b] | TON | TOF ($h^{-1}$) |
|---|---|---|---|---|---|---|---|---|---|
| 1 | Me | $YCl_3$/(1) | TBAB/(1) | 25 | 0.1 | 3 | 50 | 50 | 16.7 |
| 2 | Me | $YCl_3$/(0.5) | TBAB/(1) | 25 | 0.1 | 3 | 27 | 54 | 18.0 |
| 3 | Me | $YCl_3$/(0.1) | TBAB/(0.13) | 100 | 1 | 0.75 | 80 | 800 | 1067 |
| 4 | Me | $YCl_3$/(0.5) | DMAP/(1) | 40 | 0.2 | 12 | 50 | 50 | 4.2 |
| 5 | Ph | $Y_2O_3$/(0.3) | PPNCl/(0.3) | 120 | 1 | 3 | 88 | 270 | 90 |
| 6 | Me | $Y(NO_3)_3$/(0.5) | TBAB/(0.5) | 60 | 0.5 | 6 | 27 | 54 | 9.0 |
| 7 | Me | $ScCl_3$/(0.5) | TBAB/(1) | 25 | 0.1 | 3 | 55 | 110 | 36.7 |
| 8 | Me | $LaCl_3$/(0.5) | TBAB/(1) | 25 | 0.1 | 6 | 10 | 20 | 3.3 |
| 9 | $CH_2Cl$ | $YCl_3$/(1) | TBAB/(2) | 22 | dynamic | 5 | 33 | 33 | 6.6 |

[a]TBAB = Tetra-n-butylammonium bromide, DMAP = 4-dimethylaminopyridine, PPNCl = Bis(triphenylphosphine)iminium chloride.
[b]Determined by $^1$H NMR by integration of the starting material and product signals for the corresponding protons.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding based on numerical value and the measurement techniques. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method comprising, performing the following reaction shown below:

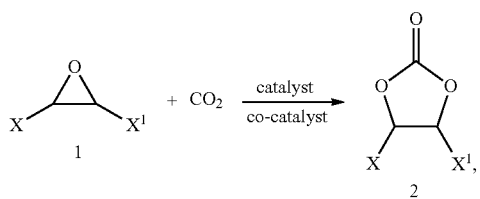

wherein X is selected from the group consisting of: a linear or branched, substituted or unsubstituted alkyl group; a substituted or unsubstituted aryl group; a substituted or unsubstituted heteroaryl group;

wherein $X^1$ is H;

wherein the catalyst is $YCl_3$, $Y_2O_3$, $Y(NO_3)_3$, $ScCl_3$, or $LaCl_3$;

wherein $CO_2$ represents $CO_2$ or a mixture of gases containing $CO_2$, and wherein the cocatalyst is selected from the group consisting of: tetrabutylammonium bromide, 4-dimethylaminopyridine, or bis(triphenylphosphine) iminium chloride.

2. The method of claim 1, further comprising conducting the reaction at a partial pressure of about 0.001 MPa to about 20 MPa of $CO_2$, and wherein the temperature of the reaction is from about −50° C. to about 250° C.

3. The method of claim 1, wherein $CO_2$ or a mixture of gases containing $CO_2$ is continuously added to the reaction mixture under dynamic conditions.

4. The method of claim 1, wherein the catalyst is $YCl_3$ and the co-catalyst is tetrabutylammonium bromide.

5. The method of claim 1, wherein the catalyst is $YCl_3$ and the co-catalyst is 4-dimethylaminopyridine.

6. The method of claim 1, wherein the catalyst is $Y_2O_3$ and the co-catalyst is bis(triphenylphosphine) iminium chloride.

7. The method of claim 1, wherein the catalyst is $Y(NO_3)_3$ and the co-catalyst is tetrabutylammonium bromide.

8. The method of claim 1, wherein the catalyst is $ScCl_3$ and the co-catalyst is tetrabutylammonium bromide.

9. The method of claim 1, wherein the catalyst is $LaCl_3$ and the co-catalyst is tetrabutylammonium bromide.

* * * * *